United States Patent [19]
Seiler

[11] Patent Number: 4,692,453
[45] Date of Patent: Sep. 8, 1987

[54] PHARMACEUTICAL ACTIVE 1,2,3,4,4A,5,10,10A-OCTAHYDROBENZO[G]QUINOLINE DERIVATIVES, AND THEIR USE

[75] Inventor: Max P. Seiler, Basle, Switzerland
[73] Assignee: Sandoz Ltd., Basel, Switzerland
[21] Appl. No.: 797,563
[22] Filed: Nov. 13, 1985

Related U.S. Application Data

[63] Continuation of Ser. No. 573,513, Jan. 25, 1984, abandoned.

[30] Foreign Application Priority Data

Feb. 1, 1983 [CH] Switzerland ............................ 560/83

[51] Int. Cl.$^4$ ..................... A61K 31/47; C07D 221/08
[52] U.S. Cl. ..................................... 514/290; 546/101
[58] Field of Search ......................... 546/101; 514/290

[56] References Cited

U.S. PATENT DOCUMENTS 3,639,411  2/1972  Alberston et al. ............... 546/101 X
3,839,338  10/1974  Albertson et al. ............... 546/101 X
3,898,235  8/1975  Albertson et al. .................. 546/101
4,565,818  1/1986  Nordmann et al. .................. 514/290

FOREIGN PATENT DOCUMENTS 0077754  4/1983  European Pat. Off. ............ 546/101

OTHER PUBLICATIONS

Walsh et al., J. Org. Chem., vol. 39, No. 25, pp. 3705–3708 (1974).
Cannon et al., Chemical Abstracts, vol. 92, 51846n (1980).
Cannon et al., Chemical Abstracts vol. 94, 83909t (1981).
Costall et al., Chemical Abstracts, vol. 95, 161968y (1981).
Cannon et al., Chemical Abstracts, vol. 96, 6539m (1982).
Maixner et al., Chemical Abstracts, vol. 98, 172567e (1983).
Cannon et al., Chemical Abstracts, vol. 100, 51426j (1984).

Primary Examiner—Nicholas S. Rizzo
Assistant Examiner—Diana G. Rivers
Attorney, Agent, or Firm—Gerald D. Sharkin; Robert S. Honor; Thomas O. McGovern

[57] ABSTRACT

A 6- or 8-monooxy- or 6,8-dioxy-1,2,3,4,4a,5,10,10a-octahydrobenzo[g]quinoline in which the 3-position is unsubstituted, is useful as a pharmaceutical, in particular as a prolactin secretion inhibitor, dopaminergic agent and dopamine receptor stimulating agent.

7 Claims, No Drawings

PHARMACEUTICAL ACTIVE 1,2,3,4,4A,5,10,10A-OCTAHYDROBENZO[G] QUINOLINE DERIVATIVES, AND THEIR USE

This is a continuation of application Ser. No. 573,513, filed Jan. 25, 1984 now abandoned.

The present invention relates to novel 1,2,3,4,4a,5,10,10a-octahydro-benzo[g]quinoline derivatives having valuable pharmaceutical properties, processes for the production of said derivatives, pharmaceutical compositions comprising said derivatives and the use of said derivatives as pharmaceuticals.

1,2,3,4,4a,5,10,10a-trans-octahydrobenzo[g]-quinoline derivatives, which are unsubstituted in position 3 and having in both the positions 6 and 7 or both the positions 7 and 8 a hydroxy group, are known from Proc. 7th. Int. Symp. Med. Chem. 1980, Pergamon Press 1981, p. 369–381, especially the corresponding 1-N-H, 1-N-methyl, 1-N-ethyl and 1-N-propyl compounds.

It was reported that the 1-N-H and 1N-alkyl-6,7-dihydroxy compounds generally have a dopaminergic activity, of which the 1N-H compound has the weaker and the 1-N-propyl compound has the stronger activity (p. 374–376), whereas the corresponding 1-N-H and 1-N-alkyl-7,8-dihydroxy compounds have no dopaminergic activity (p. 371).

1,2,3,4,4a,5,10,10a-trans-octahydrobenzo[g]quinoline derivatives, which are unsubstituted in position 3 and substituted in both positions 6 and 7 with a methoxy group, especially the corresponding 1-N-H, the 1-N-methyl, the 1-N-ethyl and the 1-N-propyl compounds, are known from J. Heterocycl. Chem. 17, p. 1633–1636 (1980), especially p. 1634 and 1635. No pharmacological activities are mentioned.

1,2,3,4,4a,5,10,10a-cis-octahydrobenzo[g]quinolines which are unsubstituted in position 3 and substituted in position 7 with a hydroxyl group, especially the 1-N-methyl and the 1-N-propyl compounds, are known from J. Med. Chem. 1976, Vol. 19, p. 1159–1161, especially p. 1160, and U.S. Pat. No. 3,898,235 (Ex. 42 and 46) and are reported to have analgesic antagonist properties.

1,2,3,4,4a,5,10,10a-cis- and trans-octahydrobenzo[g]quinoline derivatives, unsubstituted in position 3 and substituted in position 7 by a hydroxyl group, e.g. the corresponding 1-N-H, the 1-N-CH$_3$ and the 1-N-propyl compounds are known from the U.S. Pat. No. 3,839,338 (Ex. 39,41, 42 and 46). They are also reported to have analgesic antagonist properties.

It is appreciated that from the prior art citation above, especially from the first citation, no prediction can be made as to pharmacological profile in relation to the position and the number of oxy group containing substituents in the benzene ring.

The present invention provides a 6- or 8-mono oxy- or 6,8-dioxy-1,2,3,4,4a,5,10,10a-octahydro-benzo[g]quinoline in which the 3-position is unsubstituted, hereinafter indicated as a compound of the invention. These compounds have advantageous properties in comparison to the known compounds discussed above and neither the compounds of the invention nor their advantageous properties are in any way suggested by the prior art discussed.

The benzo[g]quinoline nucleus of the compounds in accordance with the invention may bear further substituents, i.e. in addition to those defined above at the 6- and/or 8-positions, however with the exception of the 3-position. Preferred benzo[g]quinolines in accordance with the invention are those, in which the 1-position is unsubstituted or substituted by (C$_{1-5}$)alkyl, (C$_{3-5}$)alkinylalkyl or (C$_{3-6}$)cycloalkyl-(C$_{1-3}$)alkyl, especially in which the 1-position is unsubstituted or substituted by (C$_{1-5}$)alkyl. Suitably no further additional substituents beyond that at the 1-position are present. The oxy group(s) in the 6- and/or 8-position are suitably hydroxy or alkoxy. The hydroxy compounds may be in the form of physiologically hydrolysable and acceptable esters.

Especially preferred in accordance with the present invention are benzo[g]quinolines of formula I,

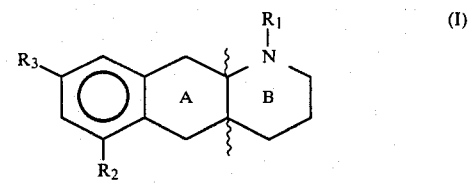

wherein
the rings A and B are cis- or trans-fused and
wherein
R$_1$ is H, (C$_{1-5}$)alkyl, (C$_{3-5}$)alkinylalkyl or (C$_{3-6}$)cycloalkyl-(C$_{1-3}$)alkyl and
R$_2$ and R$_3$ are each independently hydrogen, hydroxy, or (C$_{1-5}$)alkoxy, with the proviso that R$_2$ and R$_3$ may not both be hydrogen;
and, when one or both of R$_2$ and R$_3$ is hydroxy, physiologically-hydrolysable and -acceptable esters thereof.

By the term "physiologically-hydrolysable and -acceptable esters" are meant esters with acids which are hydrolysable under physiological conditions to yield acids which are themselves physiologically acceptable, i.e. which are non-toxic at the desired dosage levels. The esters may be obtained by acylation of benzo[g]quinolines in accordance with the invention bearing one or more hydroxy residues at the 6- and/or 8-position. The esters include esters with mono- and di-carboxylic acids in particular carboxylic acids having 1 to 5 carbon atoms.

(C$_{3-5}$)alkinylalkyl is preferably allyl and (C$_{3-6}$)cycloalkyl(C$_{1-3}$)alkyl is preferably cyclopropylmethyl.

One group of compounds in accordance with the present invention comprises benzo[g]quinolines of formula I as illustrated above, wherein
R$_1$ is hydrogen or (C$_{1-5}$)alkyl, preferably (C$_{1-5}$)alkyl, especially propyl,
R$_2$ is hydroxy or (C$_{1-5}$)alkoxy and R$_3$ is hydrogen,
and, if R$_2$ is hydroxy, physiologically-hydrolysable and -acceptable esters thereof.

A second group of compounds in accordance with the present invention comprises benzo[g]quinolines of formula I as illustrated above, wherein
R$_1$ is hydrogen or (C$_{1-5}$)alkyl,
R$_2$ is hydrogen and R$_3$ is hydroxy or (C$_{1-5}$)alkoxy, especially hydroxy,
and, if R$_3$ is hydroxy, physiologically-hydrolysable and -acceptable esters thereof.

The compoounds of the present invention exist in free and in salt form, e.g. as acid addition salts or, if at least one of R$_2$ and R$_3$ is hydroxy, in basic salt form. The present invention includes both free and salt, in particular pharmaceutically acceptable salt, forms. Examples of appropriate pharmaceutically acceptable acid addition salt forms include e.g. the hydrochlorides and the maleates. Pharmaceutically acceptable salts with bases include e.g. the sodium salts.

Since the rings A and B in formula I are cis- or trans-fused, whereby hydrogen atoms at the 4a- and 10a-positions are cis, resp. trans to each other, the compounds of the invention exist in four isomeric forms comprising two enantiomeric pairs. It will be understood that the present invention includes individual isomers, as well as racemates and other isomeric mixtures.

For pharmaceutical application individual isomers and racemates of the compounds of the invention are preferred.

In addition to the foregoing, there are also provided processes for the production of the compounds of the invention.

Particularly a process for the production of the compounds of formula I or their physiologically hydrolysable and -acceptable esters, in free or salt form is provided which process comprises:

(a) for the production of a compound of formula Ia,

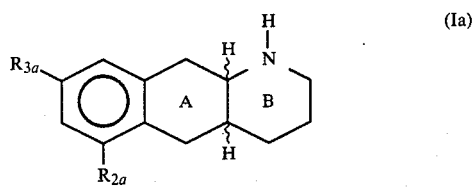

wherein
the rings A and B are cis- or trans-fused and
wherein
$R_{2a}$ and $R_{3a}$ are each independently hydrogen or $(C_{1-5})$alkoxy with the provisio that $R_{2a}$ and $R_{3a}$ may not both be hydrogen,
hydrogenating a corresponding compound of formula II,

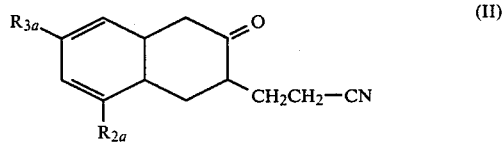

in which $R_{2a}$ and $R_{3a}$ are as defined above, (b) for the production of a compound of formula Ib,

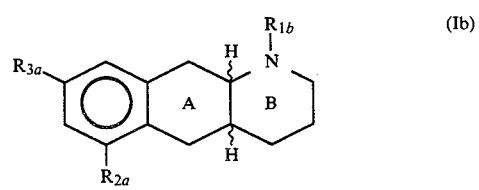

wherein the rings A and B are cis- or trans-fused, $R_{1b}$ is $(C_{1-5})$alkyl, $(C_{3-5})$alkinylalkyl or $(C_{3-6})$cycloalkyl$(C_{1-3})$alkyl and $R_{2a}$ and $R_{3a}$ are as defined above, alkylating a compound of formula Ia, (c) for the production of a compound of formula Ic,

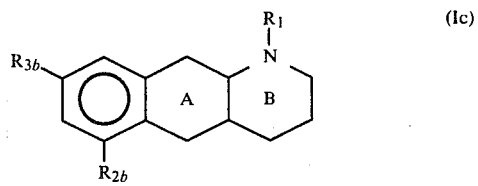

wherein
the rings A and B are cis- or trans-fused and
wherein
$R_1$ is as defined above and
$R_{2b}$ and $R_{3b}$ are hydrogen or hydroxy, with the proviso that $R_{2b}$ and $R_{3b}$ are not both hydrogen, by ether splitting of a corresponding compound of formula Ia or Ib, defined above, optionally converting a resulting compound of formula Ic into a physiologically-hydrolysable and -acceptable ester by acylation and recovering the resulting product in free or salt form.

Processes (a) to (c) above may be carried out in accordance with standard techniques known in the art.

For process (a) the hydrogenation may suitably be carried out in the presence of platinum oxide as a catalyst and e.g. in absolute ethanol as a solvent. Preferably some chloroform is added. In the reaction the starting material II is cyclisized, furnishing mainly the trans isomer of formula Ia and to a minor extent the cis isomer. Both isomer types can be separated by methods known per se, e.g. chromatography on silica gel.

The ether cleavage process (c) may be effected e.g. by reaction with HBr, BBR$_3$ or NaSCH$_3$, in the presence of an inert, organic solvent or diluent such as methylene dichloride or DMF. The reaction is suitably carried out at temperatures of from e.g. −70° to 0° C. (HBr or BBr$_3$) or from 100° to reflux (NaSCH$_3$).

The alkylation process (b) may be effected by direct alkylation or by reductive alkylation.

Direct alkylation may be effected e.g. by reaction with a compound of formula $R_{1b}$—Q, wherein Q is a leaving group. Suitable leaving groups Q include chlorine, bromine and iodine as well as organic sulfonic acid residues such as methyl- and p-toluene-sulfonyloxy residues. The reaction is preferably carried out in the presence of an acid binding agent, for example an alkali-metal or alkaline-earth metal carbonate, and of an inert organic solvent or diluent such as dimethylformamide.

Reductive alkylation may be effected e.g. by reaction with an aldehyde of formula $R_{1c}$CHO, wherein $R_{1c}$ is hydrogen or $(C_{1-4})$alkyl and with concomitant hydrogenation e.g. in the presence of an appropriate catalyst such as palladium on charcoal. The reaction is suitable carried out in the presence of an inert, organic solvent or diluent, for example the corresponding alcohol of formula $R_{1c}$CH$_2$OH, with normal or slightly elevated pressure.

The starting materials for use in the above processes (b) and (c), i.e. the compounds of formula Ia and Ib, exist in the varius isomeric forms discussed in relation to the compounds of the invention. Each of the above processes may be carried out using starting materials in the form of one or other of the individual enantiomers, or in the form of mixtures, in particular racemic mixtures thereof. Conveniently the starting materials Ia and Ib are in racemic form.

Where diastereomeric mixtures of the starting materials are used, the products too will be in the form of a diastereomeric mixture. Diastereomers may be separated, e.g. chromatographically, to yield racemates free of diastereomeric contaminants. Obtained racemates may be resolved to obtain individual optically active enantiomers using known resolution techniques for example via formation of acid addition salts with optically active acids and resolution of the obtained diastereomeric salt.

The compounds of the invention may be recovered from the initially obtained reaction medium in free form or in salt form, e.g. in acid addition salt form. Alternatively initially obtained salts may be converted into the free form or vice versa.

The compounds of formula II may be obtained in accordance with known techniques, e.g. from 3-carbomethoxy-tetralon-2 compounds in accordance with the following reaction sequence.

TABLE 1

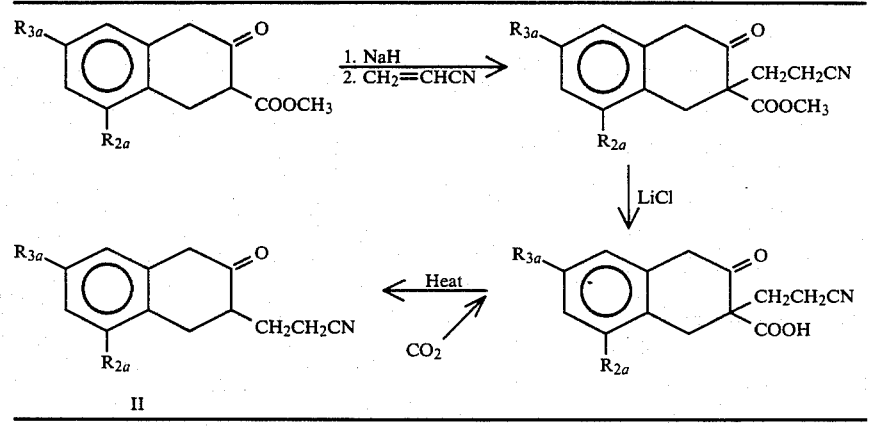

described in Proc. 7th. Int. Symp. Med. Chem. 1979, Pergamon Press. 1980, p. 369–381, for a compound of formula II in which both $R_{2a}$ and $R_{3a}$ are methoxy.

The compounds of the invention other than those of formula I may be produced in manner analogous to that described for the compounds of formula I.

The following examples in which temperatures are in degrees Centigrade are illustrative of the above described processes for the preparation of the compounds of the invention.

EXAMPLE 1

Trans-1,2,3,4,4a,5,10,10a-octahydro-6-methoxybenzo[g]quinoline 6,6 g of 3-(2-cyanoethyl)-5-methoxy-2-tetralone (described in Synth. Comm. 9 (9) 819–824 (1979)) are dissolved in 150 ml of ethanol and 10 ml of chloroform. 0.6 g of platinum oxide are added. While agitating, the suspension is hydrogenated for 22 hours at an initial pressure of 35 pounds per square inch (=2,46 kg/cm$^2$).

The mixture is filtered and concentrated and the obtained residue is extracted with an aqueous 1N sodium bicarbonate solution and with methylene chloride. After washing, drying and concentrating of the organic phase, an oil is obtained, which is purified by chromatography on silica gel, using methylene chloride (10%, saturated with ammonia)/methanol, (8/2 vol/vol) as an eluant.

The title product is obtained as the main substance, which is crystallised in methanol/ether; m.p. 227°–280° (hydrochloride salt).

$^1$H-NMR (360 MHz, CDCl$_3$): $\delta H_{C10a}=2.6$ ppm (t/d, J. ca 10 resp. 4 Hz).

EXAMPLE 2

Cis-1,2,3,4,4a,5,10,10a-octahydro-6-methoxybenzo[g]quinoline

In the chromatographic purification process of Example 1 an additional compound is isolated, identified as the corresponding cis compound.

It is crystallized in methanol/ether. m.p. 212°–214°.
$^1$H-NMR (360 MHz, CDCl$_3$): $\delta H_{C10a}=3.0$ ppm (m)

EXAMPLE 3

Trans-1,2,3,4,4a,5,10,10a-octahydro-6-hydroxybenzo[g]quinoline 2,5 g of trans-1,2,3,4,4a,5,10,10a-octahydro-6-methoxybenzo[g]quinoline are dissolved in 100 ml (47% weight) hydrobromic acid and the mixture is refluxed for 3 hours under a nitrogen atom.

The solution is concentrated in vacuum and the residue is extracted with an aqueous 1N-sodium carbonate solution and with methylene chloride-ethanol 9:1 (vol/vol). The organic phase is washed with a sodium chloride solution, dried over sodium sulphate and is concentrated to yield the solid raw material as a free base. The free base is taken up in methanol. To the mixture is added 1 equivalent of an etheric hydrochloric acid solution.

The title compound is precipitated by addition of ether as the hydrochloride salt, which is recrystallised in methanol/ether. M.p. 274°–276°.

EXAMPLE 4

Trans-1,2,3,4,4a,5,10,10a-octahydro-6-methoxy-N-n-propylbenzo[g]quinoline 3 g of trans-1,2,3,4,4a,5,10,10a-octahydro-6-methoxybenzo[g]quinoline are dissolved in 100 ml of dimethylformamide. 3.8 g potassium carbonate and 1.8 ml of n-propyl iodide are subsequently added and the obtained suspension is stirred for 2 days at room temperature.

The reaction mixture is filtered, concentrated, and the obtained oil is purified by chromatography on silica gel with methylene chloride (10% saturated with ammonia)/methanol 98/2 (vol/vol) as an eluant. The solid

EXAMPLE 5

Trans-1,2,3,4,4a,5,10,10a-octahydro-6-hydroxy-N-n-propylbenzo[g]quinoline 1.6 g of trans-1,2,3,4,4a,5,10,10a-octahydro-6-methoxy-N-n-propylbenzo[g]quinoline are dissolved in 100 ml of methylene chloride. 1.5 ml of boron tribromide, dissolved in 20 ml of methylene chloride are added dropwise and the mixture is stirred for 1.5 hours at room temperature. An excess of methanol is added to the mixture which is then concentrated in vacuum. This is repeated twice.

The final residue is extracted with an aqueous 1N sodium carbonate solution and with methylene chloride. After washing, drying and concentration of the organic phase, the title compound is obtained in the form of the solid free base.

The hydrochloride salt is recrystallised from methanol/ether. M.p. 342°–345°.

EXAMPLE 6

Trans-1,2,3,4,4a,5,10,10a-octahydro-N-methyl-6-methoxybenzo[g]quinoline 3,2 g of trans-1,2,3,4,4a,5,10,10a-octahydro-6-methoxybenzo[g]-quinoline are dissolved in 35 ml of methanol.

To the solution of 23.5 ml of an aqueous formaldehyd solution and 0.5 g of Pd/C (10%) are added, after which the mixture is hydrogenated.

The catalyst is removed by filtration and the mixture is extracted with an 1N aqueous sodiumbicarbonate solution and with methylene chloride. The organic phases are collected and dried, concentrated and purified by chromatography on silicagel, using methylene chloride (10%, saturated with ammonia)/methanol (95/5vol/vol) as an eluant.

The obtained trans compound has a m.p. of 257°–259° (Hydrochloride).

EXAMPLE 7

Cis-1,2,3,4,4a,5,10,10a-octahydro-N-methyl-6-methoxybenzo[g]quinoline

In the chromatographic purification process of Example 6 additionally the corresponding cis-compound is obtained, having a m.p. of 217°–219° (Hydrochloride).

EXAMPLE 8

Trans-1,2,3,4,4a,5,10,10a-octahydro-N-methyl-6-hydroxybenzo[g]quinoline

This compound is obtained from the title compound of Example 6, analogously to Example 3 and 5. M.p. 323°–325° (Hydrochloride).

EXAMPLE 9

Cis-1,2,3,4,4a,5,10,10a-octahydro-N-methyl-6-hydroxybenzo[g]quinoline

This compound is obtained from the title compound of Example 7, analogously to Example 5 and 3. M.p. 256°–258° (Hydrochloride).

The following compounds of formula I are obtained analogously to Examples 1 to 9.

TABLE 2

| Ex. No. | $R_1$ | $R_2$ | $R_3$ | ring connection | M.p. | Prepared analogously to Ex. No (process) |
|---|---|---|---|---|---|---|
| 10 | $C_2H_5$ | $OCH_3$ | H | trans | 166–168° (HCl salt) | Ex. 6 (b) |
| 11 | $C_2H_5$ | OH | H | trans | 326–327° (HCl salt) | Ex 8 (c) |

The following compounds of formula I are prepared according to process (a) from corresponding compounds of formula II in table 1, wherein $R_{2a}$ is hydrogen and $R_{3a}$ is methoxy, (Ex 12) and additional processes (b) or (c), (Ex 13–18).

TABLE 3

| Ex. No. | $R_1$ | $R_2$ | $R_3$ | ring connection | M.p. | Prep. from Ex. No. (process) |
|---|---|---|---|---|---|---|
| 12[1] | H | H | $OCH_3$ | trans | | |
| 13[2] | H | H | OH | cis | | |
| 14 | H | H | OH | trans | 312–314° (HCl salt) | Ex 12 (c) |
| 15 | $CH_3$ | H | $OCH_3$ | trans | | Ex 12 (b) |
| 16 | $CH_3$ | H | OH | trans | 274–275° (HCl salt) | Ex 15 (c) |
| 17 | n-propyl | H | $OCH_3$ | trans | | Ex 12 (b) |
| 18 | n-propyl | H | OH | trans | 255–260° (HCl salt) | Ex 17 (c) |

[1] by process (a)
[2] by process (a) and subsequent process (c)

The compounds of the invention possess pharmacological properties as indicated in animal tests and are accordingly useful as pharmaceuticals.

In particular, they exhibit prolactin secretion inhibiting activity as indicated by inhibition of pregnancy (ovum implantation) on administration to female rats on the 5th day after insemination, at dosages of from 0.01 to 3.0 mg/kg s.c., as well as by reduction of serum prolactin levels as measured by RIA, 4 hours after administration to male rats at dosages of from 0.001 to 0.1 mg/kg s.c. [both tests carried out in accordance with the methods described in Experientia 34, 1330 (1978)].

The compounds of the invention are accordingly useful as prolactin secretion inhibitors, e.g. in the treatment of conditions or disorders for which reduction of prolactin secretion levels is indicated, for example for the treatment of galactorrhoea including post-partum galactorrhoea, for the treatment of prolactin-dependent menstrual disorders including amenorrhoea, for the inhibition of lactation including post-partum lactation and morbid lactation as well as for the treatment of hyperprolactinaemic hypogonadism in males and females and of prolactinoma.

For this use the dosage will of course vary depending on e.g. the particular compound employed, the mode of administration, the particular condition to be treated and the effect desired. However, in general satisfactory results are obtained on administration at daily dosages of from about 0.004 to about 0.15 mg/kg body weight, conveniently given in divided doses 2 to 4 times a day or in sustained release form. For larger mammals, the total daily dosage is in the range of from about 0.25 to about 10 mg and suitable unit dosage forms, e.g. for oral administration, comprise from about 0.05 to about 5 mg of active ingredient together with a pharmaceutically acceptable diluent or carrier therefor.

As already indicated the daily dosages suitable for any particular compound will depend on a number of factors including its relative potency of activity. For the compounds of examples 4 and 5, which are most preferred compounds in accordance with the present invention, the determined $ED_{50}$ in the ovum implantation test described above is 0.02 mg/kg. For the known prolactin secretion inhibitor bromocriptine, a determined $ED_{50}$ in the same test is 0.75 mg/kg. An indicated daily dosage for the compounds of examples 4 and 5 would accordingly be of the order of from about 1/30 to about 1/10 of the daily dosage applicable in the case of brmocriptine.

In addition to the foregoing, the compounds of the invention also exhibit dopaminergic activity on the nervous system as indicated by elicited contralateral rotation on administration at dosages of from 0.05 to 2.0 mg/kg i.p. to rats in which unilateral damage of the nigro-neostriatal dopamine pathway has been induced by injection of 6-hydroxydopamine into the substantia nigra [test carried out in accordance with the method of U. Ungerstedt, Acta physiol. scand. Suppl. 367, 69–93 (1973)]. The said compounds also exhibit stereotypy in the apomorphine stereotypy test on administration at dosages of about 10 mg/kg i.p.

The compounds of the invention are accordingly also useful as dopaminergic agents e.g. for the treatment of Morbus Parkinson. For this use the dosage will, of course, vary depending on e.g. the particular compound employed, the mode of administration, the condition to be treated and the effect desired. However, in general satisfactory results are obtained on administration at daily dosages of from about 0.01 to about 0.5 mg/kg body weight, conveniently given in divided doses 2 to 4 times a day or in sustained release form. For larger mammals, the total daily dosage is in the range of from about 1 to about 40 mg and suitable until dosage forms, e.g. for oral administration comprise from about 0.25 to about 20 mg of active ingredient together with a pharmaceutically acceptable diluent or carrier therefor.

The compounds of the invention also exhibit dopamine receptor stimulating activity on the cardiovascular system as indicated by induction of decreased blood pressure and decreased superior nesenteric vascular resistance in the anaesthetised dog. B. J. Clark, Postgrad. Med. J. 57 (Suppl. 1) 45–54. For this test dogs are employed which have been anaesthetised with chloralose and urethane. Blood pressure is measured by means of a catheter inserted in the femoral artery. Blood flow in the superior mesenteric artery is measured by means of an electromagnetic flow probe. The said compounds of the invention cause a decrease in blood pressure as well as a decrease in superior mesenteric vascular resistence on administration in the above test at doses of from 10 to 100 μg/kg i.v.

The compounds of the invention are accordingly also useful as dopamine receptor stimulators e.g. for the treatment of congestive heart failure, as well as of hypertension and oliguric renal failure. For this use the dosage will of course vary depending on e.g. the particular compound employed, the mode of administration, the condition to be treated and the effect desired. However, in general satisfactory results are obtained on adminstration at daily dosages of from about 0.02 to about 10 mg/kg body weight conveniently given in divided doses 2 to 4 times a day or in sustained release form. For larger mammals, the total daily dosage is in the range of from about 1 to 500 mg and suitable unit dosage forms e.g. for oral administration comprise from about 0.25 to 250 mg of the active ingredient together with a pharmaceutically acceptable diluent or carrier therefor.

As indicated above, for administration the compounds of the invention may be in free or in pharmaceutically acceptable salt form, in particular pharmaceutically acceptable acid addition salt form. Such salt forms exhibit the same order of activity as the free forms.

Pharmaceutical compositions may be prepared employing conventional techniques known in the galenic art. Suitable galenic forms of administration include e.g. tablets and capsules.

We claim:

1. A benzo[g]quinoline of formula I

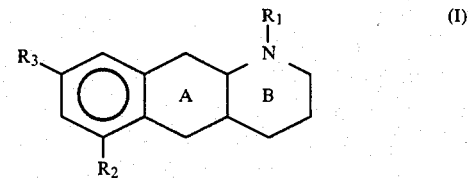

wherein
the rings A and B are trans-fused and
wherein
$R_1$ is $(C_{1-5})$alkyl,
$R_2$ is hydroxy or $(C_{1-5})$alkoxy, and
$R_3$ is hydrogen,
and when $R_2$ is hydroxy, its physiologically-hydrolysable and -acceptable esters, in free base or in pharmaceutically acceptable salt form.

2. A benzo[g]quinoline according to claim 1 wherein
$R_1$ is $(C_{1-5})$alkyl,
$R_2$ is $(C_{1-5})$alkoxy, and
$R_3$ is hydrogen in free base or pharmaceutically acceptable salt form.

3. The benzo[g]quinoline according to claim 1, which is trans-1,2,3,4,4a,5,10,10a-octahydro-6-methoxy-N-n-propyl-benzo[g]quinoline, in free base or in pharmaceutically acceptable salt form.

4. A compound according to claim 1 selected from the group comprising:
   (a) Trans-1,2,3,4,4a,5,10,10a-octahydro-6-hydroxy-N-n-propyl-benzo[g]quinoline;
   (b) Trans-1,2,3,3,4,4a,5,10,10a-octahydro-6-hydroxy-N-methyl-benzo[g]quinoline;
   (c) Trans-1,2,3,4,4a,5,10,10a-octahydro-N-ethyl-6-methoxy-benzo[g]quinoline; and
   (d) Trans-1,2,3,4,4a,5,10,10a-octahydro-N-ethyl-6-hydroxy-benzo[g]quinoline;
in free base or in pharmaceutically acceptable salt form.

5. A pharmaceutical composition useful in inhibiting prolactin secretion or in treating Morbus Parkinson, coronary disease, hypertension or oliguric renal failure comprising a therapeutically effective amount of a compound as claimed in claim 1 in free or in pharmaceutically acceptable salt form, together with a pharmaceutically acceptable diluent or carrier.

6. A method of inhibiting prolactin secretion in a subject in need of such treatment which method comprises administering to said subject an effective amount of a compound according to anyone of claims 1 in free or pharmaceutically acceptable salt form.

7. A method of treating Morbus Parkinson or coronary disease, hypertension or oliguric renal failure in a subject in need of such treatment, which method comprises administering to said subject an effective amount of a compound according to anyone of claims 1 in free or in pharmaceutically acceptable salt form.

* * * * *